United States Patent
Kitayama et al.

(10) Patent No.: US 6,475,590 B1
(45) Date of Patent: Nov. 5, 2002

(54) AMINIUM SALT OR DIIMONIUM SALT COMPOUNDS AND USE THEREOF

(75) Inventors: Yasuyuki Kitayama, Saitama (JP); Masaaki Ikeda, Tokyo (JP); Masao Ohnishi, Saitama (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/701,928

(22) PCT Filed: Jun. 21, 1999

(86) PCT No.: PCT/JP99/03289

§ 371 (c)(1),
(2), (4) Date: Dec. 4, 2000

(87) PCT Pub. No.: WO99/67200

PCT Pub. Date: Dec. 29, 1999

(30) Foreign Application Priority Data

Jun. 23, 1998 (JP) ............................. 10/176061
Jun. 30, 1998 (JP) ............................. 10/184765
Dec. 8, 1998 (JP) ............................. 10/349093

(51) Int. Cl.$^7$ ........................ B32B 3/00; C07C 255/61
(52) U.S. Cl. ...................... 428/64.8; 558/418; 558/419
(58) Field of Search ................. 558/418, 419; 428/64.8

(56) References Cited

U.S. PATENT DOCUMENTS

| | | | |
|---|---|---|---|
| 4,656,121 A | 4/1987 | Sato et al. | 430/495 |
| 5,482,822 A | * 1/1996 | Mihara et al. | 430/270.14 |
| 5,605,732 A | * 2/1997 | Mihara et al. | 428/64.8 |

FOREIGN PATENT DOCUMENTS

| | | |
|---|---|---|
| EP | 0 153 736 | 9/1985 |
| JP | 60-228194 | 11/1985 |
| JP | 63-226642 | 9/1988 |
| JP | 5-178808 | 7/1993 |

* cited by examiner

Primary Examiner—Joseph K. McKane
Assistant Examiner—Kamal Saeed
(74) Attorney, Agent, or Firm—Nields & Lemack

(57) ABSTRACT

The present invention relates to an aminium salt or diimonium salt compound that is appropriate for use, for examples, in an optical recording medium to get the good characteristics in regeneration and storage stability as well as an infrared ray screening filter to get the excellent light fastness and heat fastness; and the use thereof.

The aminium salt or diimonium salt compound comprises an aminium cation represented by the formula (1) as described below or a diimonium cation represented by the formula (2) as described below:

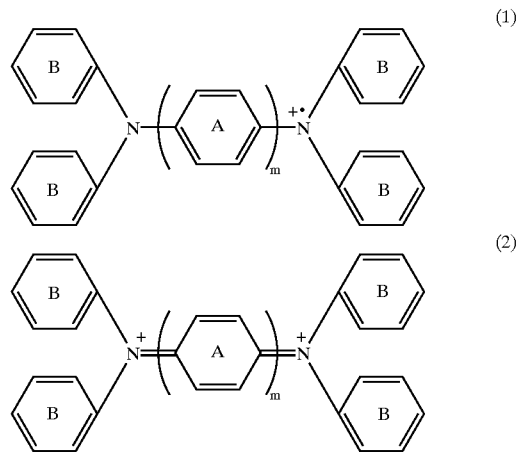

(In the formula, m is an integer of 1 or 2; the two nitrogen atoms (quaternary nitrogen atoms in Formula (2)) bound to the ring A in Formula (1) or Formula (2) bind to the four B phenyl groups to whose 4-positions the optionally substituted four amino groups are substituted; and at least one of said four amino groups has a cyanoalkyl group as the substituent) with an anion.

5 Claims, No Drawings

AMINIUM SALT OR DIIMONIUM SALT COMPOUNDS AND USE THEREOF

This is a 371 of PCT/JP99/03289 filed Jun. 21, 1999.

TECHNICAL FIELD

The present invention relates to an aminium salt or diimonium salt compound being absorptive in the infrared region, and the shaped product containing the compound, especially the optical recording medium or the infrared ray screening filter.

BACKGROUND ART

An aminium salt or a diimonium salt, the infrared absorbent, has been widely used for a heat insulating film or sunglasses. However, the salt as a dyestuff has problems in heat fastness and light fastness because it is liable to deterioration by light or heat during a production process. An organic dyestuff such as the cyan dyestuff is proposed to use for optical recording media, especially only one time writable optical disks such as CD-R and DVD-R and optical cards. They have similarly the problem that regeneration property of record and shelf stability lower because the dyestuff is liable to change by heat and light. Any dyestuff for an infrared ray screening filter or a heat ray shielding film has not yet provided to show satisfactory heat fastness, light fastness, infrared absorption and visible light transmission.

For means to solve these problems, JP Patent publication No.26028/1994 B and JP Patent Laid-Open No.99885/1989 disclosed the technique to add an aminium salt or a diimonium salt, but the technique needs another improvement because satisfactory heat fastness and light fastness remain to be realized. Under this situation, an object of the present invention is to provide an aminium salt or diimonium salt compound being more excellent in heat fastness and light fastness, and the product containing said compound, especially the optical recording medium having good light fastness and durability as well as the infrared ray screening filter having excellent heat fastness and light fastness.

DISCLOSURE OF THE INVENTION

The present inventors made a diligent study to solve the above problems. As a result, it has been found to complete the invention that a certain aminium salt or diimonium salt compound that is substituted with an amino group having the cyano-substituted alkyl group is excellent in heat fastness and light fastness.

The present invention relates to the following:
(1) An aminium salt or diimonium salt compound comprising the aminium or diimmomium cation and an anion, said aminium cation having a skeletal structure represented by Formula (1) as described below:

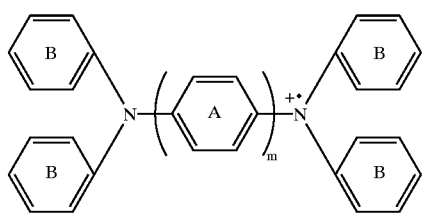

(In the formula, m is an integer of 1 or 2), said diimonium cation having a skeletal structure represented by formula (2) as described below:

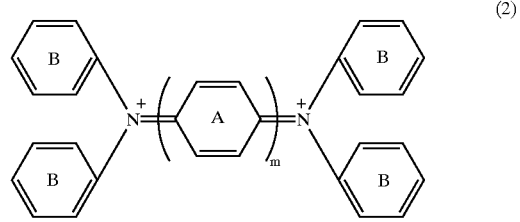

(In the formula, m is an integer of 1 or 2), where the two nitrogen atoms (quaternary nitrogen atoms in Formula (2)) bound to the ring A in Formula (1)or Formula (2) bind to the four B phenyl groups to whose 4-positions the optionally substituted four amino groups are substituted respectively; and at least one of said four amino groups has a cyanoalkyl group as the substituent.

(2) An aminium salt or diimonium salt compound according to the above (1), wherein said cyanoalkyl group is a cyano (C1–C5) alkyl group.

(3) An aminium salt or diimonium salt compound according to the above (1) or (2), wherein all of said four amino groups have their respective cyanoalkyl groups.

(4) An aminium salt or diimonium salt compound according to the above (3), wherein said amino groups having said cyanoalkyl groups are di(cyanoalkyl)amino groups.

(5) An aminium salt or diimonium salt compound according to the above (4), wherein said cyanoalkyl groups are cyanopropyl groups.

(6) A product, wherein said product contains an aminium salt or diimonium salt compound according to any of the above (1) to (5).

(7) A optical recording medium, wherein said medium contains an aminium salt or diimonium salt compound according to any of the above (1) to (5) as the recording layer.

(8) An infrared ray screening filter, wherein said infrared ray screening filter has a layer containing an aminium salt or diimonium salt compound according to any of the above (1) to (5).

(9) An infrared absorbent, wherein said infrared absorbent contains an aminium salt or diimonium salt compound according to any of the above (1) to (5) as the effective ingredient.

(10) A dyestuff stabilizer, wherein said dyestuff stabilizer contains an aminium salt or diimonium salt compound according to any of the above (1) to (5) as the effective ingredient.

(11) A cyanoalkyl substitution product of N, N, N', N'-tetrakis(aminophenyl)-p-phenylenediamine represented by Formula (6) as described below:

(6)

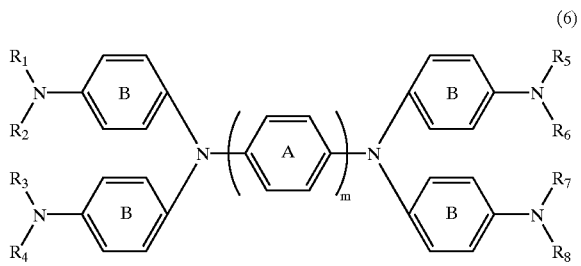

(4)

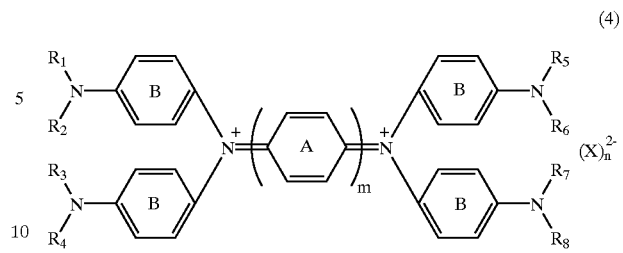

(In the formula, the ring A and B are benzene rings which may have further one to four substituents; each $R_1$ to $R_8$ is hydrogen atom or a C1–C8 alkyl group, at least one of $R_1$ to $R_8$ being a cyano-substituted alkyl group; and m is an integer of 1 or 2)

BEST MODE FOR CARRYING OUT THE INVENTION

The present invention will be described below in detail.

The aminium salt of the present invention is a salt of the aminium cation and an anion as the counterion. The aminium cation has a skeletal structure represented by the above formula (1). The skeletal structure is characterized by the following: the two quaternary nitrogen atoms bind to the four phenyl groups which have the four optionally substituted amino groups at their respective 4-positions; and at least one of said four amino groups has a cyano-substituted alkyl group as the substituent. An example of the aminium salt is represented by Formula (3) as described below:

(3)

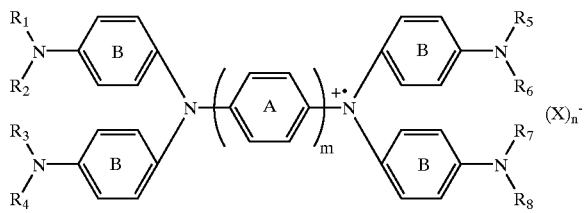

In Formula (3), m is an integer of 1 or 2, and the ring A and B are benzene rings which may have further one to four substituents, and each $R_1$ to $R_8$ is hydrogen atom or a C1–C8 alkyl group, at least one of which is a cyano-substituted alkyl group. X is an anion, and n is 1 or ½. All the other groups of $R_1$ to $R_8$ than cyano-substituted alkyl groups are preferably C1 to C8 alkyl groups.

The diimonium salt of the present invention is a salt of the diimonium cation and an anion as the counterion. The diimonium cation has a skeletal structure represented by the above formula (2). The skeletal structure is characterized by the following: the two quaternary nitrogen atoms bind to the four phenyl groups which have the four optionally substituted amino groups at their respective 4-positions; and at least one of said four amino groups has a cyano-substituted alkyl group as the substituent. An example of the diimonium salt is represented by Formula (4) as described below:

(In the formula, m is an integer of 1 or 2)

In Formula (4), m is an integer of 1 or 2, and the ring A and B are benzene rings which may have further one to four substituents, and each $R_1$ to $R_8$ is hydrogen atom or a C1–C8alkyl group, at least one of which is a cyano-substituted alkyl group. X is an anion, and n is 1 or 2. All the other groups of $R_1$ to $R_8$ than cyano-substituted alkyl groups are preferably C1 to C8 alkyl groups.

In Formula (3) and (4), the ring A has optionally 1 to 4 substituents. The substituents to bind include a halogen atom, hydroxyl group, an alkoxy group, cyano group, a lower alkyl group. The halogen atom includes fluorine atom, chlorine atom, bromine atom and iodine atom. The alkoxy group includes a C1–C5 alkoxy group such as methoxy group and ethoxy group. The lower alkyl group includes a C1–C5 alkyl group such as methyl group and ethyl group. The preferable ring A has no substituent or otherwise has a halogen atom (especially, chlorine atom or bromine atom), methyl group or cyano group. The ring A, if it has two substituents, has preferably them at the 2- and 5-positions where the nitrogen atom binds to the ring A at the 1-position in the compound of Formula (3).

The other substituents of the ring B than the above amino group include a halogen atom, hydroxyl group, an alkoxy group, cyano group, a lower alkyl group. The halogen atom includes fluorine atom, chlorine atom, bromine atom and iodine atom. The alkoxy group includes a C1–C5 alkoxy group such as methoxy group and ethoxy group. The lower alkyl group includes a C1–C5 alkyl group such as methyl group and ethyl group.

Among the alkyl groups of $R_1$–$R_8$, at least one is a cyano-substituted alkyl group and the others are the C1–C8 alkyl groups that may have cyano group or the other substituent, where the alkyl chains may be straight or branched and same or different each other. The cyano-substituted alkyl group includes a cyano-substituted C1–C8 alkyl group such as cyanomethyl group, 2-cyanoethyl group, 3-cyanopropyl group, 2-cyanopropyl group, 4-cyanobutyl group, 3-cyanobutyl group, 2-cyanobutyl group, 5-cyanopentyl group, 4-cyanopentyl group, 3-cyanopentyl group, 2-cyanopentyl group, 6-cyanohexyl group, 5-cyanohexyl group, 4-cyanohexyl group, 3-cyanohexyl group and 2-cyanohexyl group. The preferable examples have an alkyl carbon number of 2–5, and the more preferable one includes cyanopropyl group. The alkyl groups of $R_1$–$R_8$ includes methyl group, ethyl group, n-propyl group, isopropyl group, n-butyl group, sec-butyl group, tert-butyl group, pentyl group, hexyl group, and heptyl group.

X is a univalent anion or a bivalent anion. The n in Formula (3) is 1 if X is a univalent anion, and ½ if X is a bivalent anion. The n in Formula (4) is 2 if X is a univalent anion, and 1 if X is a bivalent anion. The univalent anion includes an organic acid univalent anion and an inorganic univalent anion. The organic acid univalent anion includes an organic carboxylic acid ion such as acetate ion, lactate ion, trifluoroacetate ion, propionate ion, benzoate ion, oxalate ion, succinate ion and stearate ion; an organic sulfonic acid ion such as methane sulfonate ion, toluene sulfonate ion, naphthalene monosulfonate ion, chlorobenzene sulfonate ion, nitrobenzene sulfonate ion, dodecylbenzene sulfonate ion, benzene sulfonate ion, ethane sulfonate ion and trifluoromethane sulfonate ion; and an organic boric acid ion such as tetraphenylborate ion and butyltriphenylborate ion. The preferable examples include a halogenoalkylsulfonate ion and an alkylarylsulfonate ion, such as trifluoromethane sulfonate ion and toluene sulfonate ion, where the alkyl group is a C1–C8 alkyl group, preferably a C1–C5 lower alkyl group. The more preferable examples are trifluoromethane sulfonate ion and toluene sulfonate ion.

The inorganic univalent anion includes a halogenide ion such as fluoride ion, chloride ion, bromide ion, iodide ion; thiocyanate ion, hexafluoroantimonate ion, perchlorate ion, periodate ion, nitrate ion, tetrafluoroborate ion, hexafluorophosphate ion, molybdate ion, tungstate ion, titanate ion, vanadate ion, phosphate ion and borate ion. The preferable examples include perchlorate ion, iodide ion, tetrafluoroborate ion, hexafluorophosphate ion, hexafluoroantimonate ion. Among these inorganic anions, perchlorate ion, iodide ion, tetrafluoroborate ion, hexafluorophosphate ion, hexafluoroantimonate ion are particularly preferable.

The bivalent anion includes the bivalent ion of an organic acid as described below:

Naphthalene disulfonic acid derivatives such as Naphthalene-1,5-disulfonic acid, R acid, G acid, H acid; benzoyl-H acid; p-chlorobenzoyl-H acid, p-toluene sulfonyl-H acid; chloro-H acid; chloroacetyl-H acid; methanyl-γ acid; 6-sulfonaphthyl-γ acid, C acid, ε acid; p-toluenesulfonyl-R acid; naphthalene-1,6-disulfonic acid and 1-naphthol-4,8-disulfonic acid; carbonyl-J acid; 4,4'-diaminostilbene-2,2'-disulfonic acid; di J acid; naphthalic acid; naphthalene-2,3-dicarboxylic acid; diphenic acid; stilbene-4,4'-dicarboxylic acid; 6-sulfo-2-oxy-3-naphthoic acid; anthraquinone-1,8-disulfonic acid; 1,6-diaminoanthraquinone-2,7-disulfonic acid; 2-(4-sulfophenyl)-6-aminobenzotriazole-5-sulfonic acid; 6-(3-methyl-5-pyrazolonyl)-naphthalene-1,3-disulfonic acid; 1-naphthol-6-(4-amino-3-sulfo)anilino-3-sulfonic acid. The bivalent ion of a naphthalene disulfonic acid such as naphthalene-1,5-disulfonic acid and R acid is preferable.

The preferable combination of X, the ring A, the ring B and m in Formula (1) and (2) is provided when m is 1 or 2; the ring A has no substituent or otherwise has a halogen atom, a C1–C5 alkyl group, a C1–C5 alkoxy group or cyano group; the ring B has no substituent; each of $R_1$–$R_8$ is a cyano(C2–C5)alkyl group, especially 3-cyanopropyl group or 4-cyanobutyl group; and X is, for example, perchlorate ion, iodide ion, tetrafluoroborate ion, hexafluorophosphate ion, hexafluoroantimonate ion, trifluoromethane sulfonate ion, toluene sulfonate ion or naphthalene-1,5-disulfonate ion.

The examples of an aminium salt represented by Formula (3) of the present invention are shown in Table 1 to 3. In Table 1 to 3, 1,5-NpS represents 1,5-naphthalene disulfonate ion, and TsO does toluene sulfonate ion. If m is 1 and the ring A has no substituent, it is simply shown by "4H" and, if m is 2 and the ring A has no substituent, it is done by "8H". If all of $R_1$–$R_8$ are cyanoethyl groups ($CH_2CH_2CN$), it is simply shown by "4(EtCN,EtCN)" and, if one of $R_1$–$R_8$ is n-butyl group and the others are cyanopropyl groups ($CH_2CH_2CH_2CN$), it is done by "3(n-PrCN,n-PrCN) (n-PrCN,N—Bu)" and, in other cases of $R_1$–$R_8$, they are abbreviated similarly. In the column A of Table 3, (2,5) means the positions at which the ring A has substituents where the nitrogen atom binds to the ring A at the 1-position in the compound of Formula (3).

TABLE 1

| NO. | m | A | (R1, R2) (R3, R4) | (R5, R6) (R7, R8) | X | n |
|---|---|---|---|---|---|---|
| 1 | 1 | 4 H | | 4(n-PrCN, n-PrCN) | $SbF_6$ | 1 |
| 2 | 1 | 4 H | | 4(n-PrCN, n-PrCN) | $ClO_4$ | 1 |
| 3 | 1 | 4 H | | 4(n-PrCN, n-PrCN) | TsO | 1 |
| 4 | 1 | 4 H | | 4(n-PrCN, n-PrCN) | $PF_6$ | 1 |
| 5 | 1 | 4 H | | 4(n-PrCN, n-PrCN) | $BF_4$ | 1 |
| 6 | 1 | 4 H | | 4(n-PrCN, n-PrCN) | 1,5-NpS | 1/2 |
| 7 | 1 | 4 H | | 4(EtCN, EtCN) | $SbF_6$ | 1 |
| 8 | 1 | 4 H | | 4(EtCN, EtCN) | $ClO_4$ | 1 |
| 9 | 1 | 4 H | | 4(n-BuCN, n-BuCN) | $SbF_6$ | 1 |
| 10 | 1 | 4 H | | 4(n-BuCN, n-BuCN) | $ClO_4$ | 1 |
| 11 | 1 | 4 H | | 4(n-BuCN, n-BuCN) | 1,5-NpS | 1/2 |
| 12 | 1 | 4 H | 3(n-PrCN, n-PrCN) | (n-PrCN, n-Bu) | $SbF_6$ | 1 |

TABLE 2

| NO. | m | A | (R1, R2) (R3, R4) | (R5, R6) (R7, R8) | X | n |
|---|---|---|---|---|---|---|
| 13 | 1 | 4 H | 3(n-PrCN, n-PrCN) | (n-PrCN, n-Bu) | $ClO_4$ | 1 |
| 14 | 1 | 4 H | 3(n-Bu, n-Bu) | (n-Bu, n-PrCN) | $SbF_6$ | 1 |
| 15 | 1 | 4 H | 3(n-Bu, n-Bu) | (n-Bu, n-PrCN) | $ClO_4$ | 1 |
| 16 | 1 | 4 H | 3(n-Bu, n-Bu) | (n-Bu, n-BuCN) | $SbF_6$ | 1 |
| 17 | 1 | 4 H | 3(n-Bu, n-Bu) | (n-Bu, n-BuCN) | $ClO_4$ | 1 |
| 18 | 1 | Cl | | 4(n-PrCN, n-PrCN) | $SbF_6$ | 1 |
| 19 | 1 | Cl | | 4(n-PrCN, n-PrCN) | $ClO_4$ | 1 |
| 20 | 1 | Cl | | 4(n-PrCN, n-PrCN) | 1,5-NpS | 1/2 |
| 21 | 1 | Cl | | 4(EtCN, EtCN) | $ClO_4$ | 1 |
| 22 | 1 | Cl | | 4(n-BuCN, n-BuCN) | $SbF_6$ | 1 |
| 23 | 1 | Cl | | 4(n-BuCN, n-BuCN) | $ClO_4$ | 1 |
| 24 | 1 | Cl | | 4(n-BuCN, n-BuCN) | 1,5-NpS | 1/2 |

TABLE 3

| NO. | m | A | (R1, R2) (R3, R4) | (R5, R6) (R7, R8) | X | n |
|---|---|---|---|---|---|---|
| 25 | 1 | Cl | 3(n-PrCN, n-PrCN) | (n-PrCN, n-Bu) | $ClO_4$ | 1 |
| 26 | 1 | Cl | 3(n-Bu, n-Bu) | (n-Bu, n-PrCN) | $SbF_6$ | 1 |
| 27 | 1 | Cl | 3(n-Bu, n-Bu) | (n-Bu, n-BuCN) | $ClO_4$ | 1 |
| 28 | 1 | 2 Br (2, 5) | | 4(n-PrCN, n-PrCN) | $SbF_6$ | 1 |
| 29 | 1 | 2 Br (2, 5) | | 4(n-BuCN, n-BuCN) | $SbF_6$ | 1 |
| 30 | 1 | $CH_3$ | | 4(n-PrCN, n-PrCN) | $ClO_4$ | 1 |
| 31 | 1 | $CH_3$ | | 4(n-BuCN, n-BuCN) | $ClO_4$ | 1 |
| 32 | 1 | $CH_3O$ | | 4(n-PrCN, n-PrCN) | $ClO_4$ | 1 |
| 33 | 1 | 4 F | | 4(n-PrCN, n-PrCN) | $ClO_4$ | 1 |
| 34 | 1 | CN | | 4(n-PrCN, n-PrCN) | $ClO_4$ | 1 |
| 35 | 2 | 8 H | | 4(n-PrCN, n-PrCN) | $SbF_6$ | 1 |
| 36 | 2 | 8 H | | 4(n-PrCN, n-PrCN) | $ClO_4$ | 1 |
| 37 | 2 | 8 H | | 4(n-BuCN, n-BuCN) | $ClO_4$ | 1 |

The examples of an diimonium salt represented by Formula (4) of the present invention are shown in Table 4 to 6. The abbreviations in the tables are same as in Table 1 to 3.

TABLE 4

| NO. | m | A | (R1, R2) (R3, R4) | (R5, R6) (R7, R8) | X | n |
|---|---|---|---|---|---|---|
| 38 | 1 | 4 H | | 4(n-PrCN, n-PrCN) | $SbF_6$ | 2 |
| 39 | 1 | 4 H | | 4(n-PrCN, n-PrCN) | $ClO_4$ | 2 |
| 40 | 1 | 4 H | | 4(n-PrCN, n-PrCN) | TsO | 2 |
| 41 | 1 | 4 H | | 4(n-PrCN, n-PrCN) | $PF_6$ | 2 |
| 42 | 1 | 4 H | | 4(n-PrCN, n-PrCN) | $BF_4$ | 2 |
| 43 | 1 | 4 H | | 4(n-PrCN, n-PrCN) | 1,5-NpS | 1 |
| 44 | 1 | 4 H | | 4(EtCN, EtCN) | $SbF_6$ | 2 |
| 45 | 1 | 4 H | | 4(EtCN, EtCN) | $ClO_4$ | 2 |
| 46 | 1 | 4 H | | 4(n-BuCN, n-BuCN) | $SbF_6$ | 2 |
| 47 | 1 | 4 H | | 4(n-BuCN, n-BuCN) | $ClO_4$ | 2 |

TABLE 4-continued

| NO. | m | A | (R1, R2) | (R3, R4) (R5, R6) (R7, R8) | X | n |
|---|---|---|---|---|---|---|
| 48 | 1 | 4 H | | 4(n-BuCN, n-BuCN) | 1,5-NpS | 1 |
| 49 | 1 | 4 H | 3(n-PrCN, n-PrCN) | (n-PrCN, n-Bu) | SbF$_6$ | 2 |

TABLE 5

| NO. | m | A | (R1, R2) | (R3, R4) (R5, R6) (R7, R8) | X | n |
|---|---|---|---|---|---|---|
| 50 | 1 | 4 H | 3(n-PrCN, n-PrCN) | (n-PrCN, n-Bu) | ClO$_4$ | 2 |
| 51 | 1 | 4 H | 3(n-Bu, n-Bu) | (n-Bu, n-PrCN) | SbF$_6$ | 2 |
| 52 | 1 | 4 H | 3(n-Bu, n-Bu) | (n-Bu, n-PrCN) | ClO$_4$ | 2 |
| 53 | 1 | 4 H | 3(n-Bu, n-Bu) | (n-Bu, n-BuCN) | SbF$_6$ | 2 |
| 54 | 1 | 4 H | 3(n-Bu, n-Bu) | (n-Bu, n-BuCN) | ClO$_4$ | 2 |
| 55 | 1 | Cl | | 4(n-PrCN, n-PrCN) | SbF$_6$ | 2 |
| 56 | 1 | Cl | | 4(n-PrCN, n-PrCN) | ClO$_4$ | 2 |
| 57 | 1 | Cl | | 4(n-PrCN, n-PrCN) | 1,5-NpS | 1 |
| 58 | 1 | Cl | | 4(EtCN, EtCN) | ClO$_4$ | 2 |
| 59 | 1 | Cl | | 4(n-BuCN, n-BuCN) | SbF$_6$ | 2 |
| 60 | 1 | Cl | | 4(n-BuCN, n-BuCN) | ClO$_4$ | 2 |
| 61 | 1 | Cl | | 4(n-BuCN, n-BuCN) | 1,5-NpS | 1 |

TABLE 6

| NO. | m | A | (R1, R2) | (R3, R4) (R5, R6) (R7, R8) | X | n |
|---|---|---|---|---|---|---|
| 60 | 1 | Cl | | 4(n-BuCN, n-BuCN) | ClO$_4$ | 2 |
| 61 | 1 | Cl | | 4(n-BuCN, n-BuCN) | 1,5-NpS | 1 |
| 62 | 1 | Cl | 3(n-PrCN, n-PrCN) | (n-PrCN, n-Bu) | ClO$_4$ | 2 |
| 63 | 1 | Cl | 3(n-Bu, n-Bu) | (n-Bu, n-PrCN) | SbF$_6$ | 2 |
| 64 | 1 | Cl | 3(n-Bu, n-Bu) | (n-Bu, n-BuCN) | ClO$_4$ | 2 |
| 65 | 1 | 2 Br (2, 5) | | 4(n-PrCN, n-PrCN) | SbF$_6$ | 2 |
| 66 | 1 | 2 Br (2, 5) | | 4(n-BuCN, n-BuCN) | SbF$_6$ | 2 |
| 67 | 1 | CH$_3$ | | 4(n-PrCN, n-PrCN) | ClO$_4$ | 2 |
| 68 | 1 | CH$_3$ | | 4(n-BuCN, n-BuCN) | ClO$_4$ | 2 |
| 69 | 1 | CH$_3$ | | 4(n-PrCN, n-PrCN) | ClO$_4$ | 2 |
| 70 | 1 | 4 F | | 4(n-PrCN, n-PrCN) | ClO$_4$ | 2 |
| 71 | 1 | CN | | 4(n-PrCN, n-PrCN) | ClO$_4$ | 2 |
| 72 | 2 | 4 H | | 4(n-PrCN, n-PrCN) | SbF$_6$ | 2 |
| 73 | 2 | 4 H | | 4(n-PrCN, n-PrCN) | ClO$_4$ | 2 |

The aminium salt or diimonium salt compound of the present invention can be obtained by carrying out the following process for example.

The amine compound represented by Formula (5):

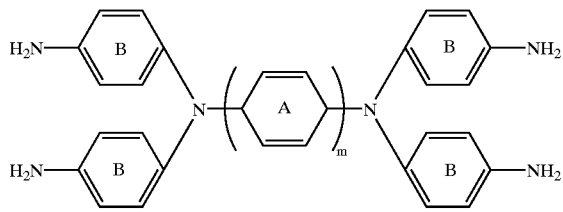

(5)

(In the formula, A, B and m are same as described above), which is previously obtained by Ullmann reaction and reduction reacton, is either reacted with a corresponding cyanoalkyl halogenide in an organic solvent, preferably in a water-soluble organic polar solvent such as DMF (dimethylformamide), DMI (dimethyl imidazolidinone) and NMP(N-methylpyrrolidone) at 30–160° C., preferably at 50–140° C. to obtain the homogenously-substituted compound, or reacted with the prescribed moles of an alkyl halogenide, followed by reacting with a corresponding cyanoalkyl halogenide to obtain the cyanoalkyl-substituted compound represented by Formula (6):

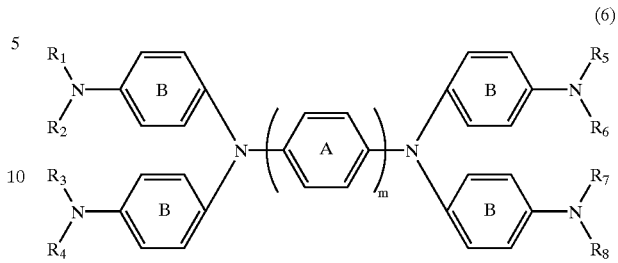

(6)

(In the formula, A, B, m and R1–R8 are same as described above)

Then, to the cyanoalkyl-substituted compound of Formula (6), the silver salt corresponding to a desired anion is added in the equal or a little more moles to the cyanoalkyl-substituted compound of Formula (6) to oxidize in an organic solvent, preferably in a water-soluble organic polar solvent such as DMF (dimethylformamide), DMI (dimethyl imidazolidinone) and NMP(N-methylpyrrolidone) at 0–100° C., preferably at 5–70° C. to obtain the aminium salt compound of the present invention. Further, the cyanoalkyl-substituted compound of Formula(6) is oxidized, in the same way as described above except that the oxidizing agent is added in the twice or a little more moles instead, to obtain the diimonium salt compound.

Alternatively, the aminium salt or diimonium salt compound of the present invention can be synthesized by oxidizing a cyanoalkyl substituted derivative of compound of Formula (5) or the cyanoalkyl-substituted compound of Formula (6) with an oxidizing agent, followed by adding the acid or the salt thereof of a desired anion in the reaction solution to promote their salt exchange.

The oxidizing agent for the above reaction is not limited to use. A metal salt such as silver nitrate, silver perchlorate and cupric chloride is preferable for the oxidizing agent.

The compound thus obtained is infrared-ray absorptive and is excellent in light fastness and heat fastness. The compound, if used in combination with an organic dyestuff, inhibits the dyestuff from deteriolating. Therefore, the compound of the present invention can be used as an infrared-ray absorbent or the stabilizer for a dyestuff, especially an organic dyestuff, by formulating with appropriate carriers or diluents if necessary. Furthermore, the compound of the present invention can be also used as an optical recording agent because it can be exposed to light to convert into a stable chemical structure that is different from the pre-exposure one, enabling an optical recording.

The shaped products containing the compound of the present invention, for examples, a film or plate-shaped resin product and the other shaped products having a resin layer containing the compound of the present invention, which is made of resin, glass, metal, ceramics or crockery, can be used as infrared ray screening filters or optical recording media.

The optical recording medium of the present invention has a recording layer on the substrate, the layer being characterized by containing the aminium salt or diimonium salt compound of the present invention. The recording layer may contain the aminium salt or diimonium salt compound of the present invention alone or in combination with various additives such as a binder. In this case, the aminium salt or diimonium salt compound of the present invention records information.

The aminium salt or diimonium salt compound of the present invention, when contained in the recording layer in which an organic dyestuff records information, can help said layer increase the light fastness. Such an optical recording medium is included in the optical recording media of the present invention.

The organic dyestuff used in combination with the aminium salt or diimonium salt compound of the present invention in the optical recording media includes a commonly known dyestuff such as a cyanine dyestuff, a squalilium dyestuff, an indoaniline dyestuff, a phthalocyanine dyestuff, an azo dyestuff, a merocyanine dyestuff, a polymethine dyestuff, a naphthoquinone dyestuff and a pyrylium dyestuff.

0.01–10 moles, preferably 0.03–3 moles of the aminium salt or diimonium salt compound of the present invention is generally used relative to 1 mole of the organic dyestuff.

The optical recording medium of the present invention has the recording layer containing the aminium salt or diimonium salt compound of the present invention and, if necessary, a desired dyestuff on the substrate, and has, if necessary, a reflective layer or a protective layer. For the substrate, a known one can be used appropriately, including a glass substrate, a metal substrate, a plastic substrate and a film. The plastic used for producing these substrates includes acryl resin, polycarbonate resin, methacryl resin, polysulfon resin, polyimide resin, noncrystaline polyolefine resin, polyester resin and polypropylene resin. The shape of substrate includes a disk, a card, a sheet and a roll film.

A guiding ditch may be prepared on the glass or plastic substrate to carry out an easy tracking. An underlaid layer made of, for example, plastic binder, inorganic oxide or inorganic sulfide may be padded on the glass or plastic substrate. The underlaid layer has preferably a lower heat transfer rate than the substrate.

The recording layer of the optical recording medium of the present invention can be produced, for example, by dissolving the aminium salt or diimonium salt compound of the present invention, preferably in combination with the other organic dyestuffs in a known solvent such as tetrafluoropropanol (TFP), octafluoropentanol (OFP), diacetone alcohol, methanol, ethanol, butanol, methyl cellosolve, ethyl cellosolve, dichloroethane, isophorone and cyclohexanone, followed by adding an appropriate binder if necessary and coating the solution on the substrate by a spin coater, a bar coater or a roll coater. Alternatively, the layer can be obtained by coating in vacuum evaporation, sputtering, docterbrading, casting or dipping the substrate in the solution. Acryl resin, urethane resin or epoxy resin for examples can be used as the binder.

The film thickness of the recording layer is preferably 0.01 $\mu$m–5 $\mu$m, more preferably 0.02 $\mu$m–3 $\mu$m in consideration of recording sensitivity or reflectance.

The optical recording medium of the present invention may have, if necessary, the underlaid layer prepared under the recording layer and the protective layer prepared over the recording layer, and may have furthermore the reflective layer prepared between the recording layer and the protective layer. The reflective layer is composed of metal such as gold, silver, copper or aluminium, preferably gold, silver or aluminium, where these metals may be used each alone or in an alloy made of two or more metals. The reflective layer can be formed into a membrane, for example, by coating in vacuum evaporation, sputtering and ion-plating. The thickness of the reflective layer is 0.02 $\mu$m–2 $\mu$m. The protective layer, if prepared, is generally formed by spincoating an ultraviolet-setting resin, followed by irradiating ultraviolet to harden the formed membrane. Epoxy resin, acryl resin, silicone resin or urethane resin for examples can be used for the material of the protective membrane. The thickness of the protective membrane is generally 0.01 $\mu$m–100 $\mu$m.

For information recording or image forming in the optical recording medium of the present invention, a condensed spot of high energy beam, i.e. a laser such as a semiconductor laser, helium-neon laser, helium-cadmium laser, YAG laser and argon laser is irradiated on the recording layer through the substrate or from the opposite site of the substrate. For information or image reading, a low power of laser beam is irradiated to determine the difference in light reflection or light transmission between a pitted portion and a non-pitted portion.

A phrase "contain the aminium salt or diimonium salt compound of the present invention" in the infrared ray screening filter of the present invention that the aminium salt or diimonium salt compound of the present invention is contained not only to exist inside the substrate but also to be sandwiched between the adjoining substrates if coated over their surfaces.

A method for producing the infrared ray screening filter using the aminium salt or diimonium salt compound of the present invention is not particularly limited, and the following methods for examples are applicable:

(1) The aminium salt or diimonium salt compound of the present invention is blended in resin, followed by molding by heat to form into a resin plate or film.

(2) The aminium salt or diimonium salt compound of the present invention is mixed with resin monomer or the prepolymer thereof, followed by polymerizing in casting under the presence of a polymerization catalyst to form into a resin plate or film.

(3) The aminium salt or diimonium salt compound of the present invention is made to contain in a coating material, followed by coating over a transparent resin plate, a transparent film or a transparent glass plate.

(4) The aminium salt or diimonium salt compound of the present invention is made to contain in an adhesive, followed by producing a laminated resin plate, a laminated resin film or a laminated glass plate.

In the method (1), the resin as a base includes polyethylene, polystyrene and polyacrylic acid. The compound of the present invention is, for example, added in powdered or pelletized base resin to dissolve by heating at 150–350° C., followed by molding to form into a resin plate. The amount of the aminium salt or diimonium salt compound represented by Formula (1) of the present invention to add is generally 0.01–30% by weight, preferably 0.03–15% by weight relative to the binder resin, though it depends on the thickness, absorption intensity and visible-ray transmittance of a resin plate or film to mold.

In the method (2), the resin to form includes acryl resin, epoxy resin and polystyrene resin. Methyl methacylate is particularly preferable because it can be bulk-polymerized in casting to give an acryl sheet that is excellent in hardness, heat fastness and chemical resistance. When the resin is produced by thermal polymerization, a known initiator can be used as the catalyst, where the polymerization is generally carried out at 40–200° C. for about 3 min to 8 hrs. Alternatively, photopolymerization can be applied with the initiator or the sensitizer added. This additive is used in 0.01–30% by weight, preferably 0.03–15% by weight relative to the above resin.

In the method (3), the aminium salt or diimonium salt compound of the present invention is, for example, dissolved in a binder resin and an organic solvent to prepare a coating material. A resin such as aliphatic ester resin and acrylic resin can be used f or the binder. A solvent such as halogenide, alcohol, ketone and ester or the mixed solvent thereof can be used for the solvent. The concentration of the aminium salt or diimonium salt compound of the present invention is generally 0.1–30% by weight relative to the binder resin, though it depends on the thickness, absorption intensity and visible-ray transmittance of a membrane to coat. The coating material thus prepared can be coated over the transparent resin film or the transparent resin plate by a spin-coater, a bar-coater, a roll-coater or a spray. The thickness of the coated membrane is generally 0. 1–500 µm, preferably 1–100 µm.

In the method (4), a common adhesive for resin such as silicon type, urethane type and acryl type or a common transparent adhesive f or a laminated glass can be used. By using the adhesive containing the compound of the present invention in 0.1–30% by weight, any one combination of transparent resin plate/resin plate, resin plate/resin film, resin plate/glass, resin film/resin film, resin film/glass and glass/glass can be adhered to produce the filter.

In the above methods, a common additive for plastic production such as an ultraviolet absorbent and a plasticizer may be added in blending or mixing.

To produce the infrared-ray screening filter, the aminium salt or diimonium salt compound of the present invention may be mixed with the other near-infrared absorptive compound such as a phthalocyanine dyestuff and a cyanine dyestuff. The near-infrared absorptive compound of inorganic metal includes copper metal, a copper compound such as copper sulfide and copper oxide, a metal mixture containing mainly zinc oxide, a tungsten compound, ITO (indium tin oxide) and ATO (tin oxide antimony doped).

To adjust the color tone of the filter, a dyestuff having absorption in the region of visible ray is preferably added as long as it gives no inhibition to the effect of the present invention. The filter of the present invention can be adhered to the filter containing a toning dyestuff alone.

The higher visible ray transmission of such an infrared-ray screening filter, if used for the front filter of a display, is preferable, and the infrared-ray screening filter needs to have the transmission of at least 40% or more, preferably 50% or more. The region of near-infrared ray for the filter to screen is 800–900 µm, more preferably 800–1000 µm. Therefore, the filter is desired to have an average transmission in said region of 50% or less, preferably 30% or less, more preferably 20% or less, and most preferably 10% or less.

EXAMPLE

The present invention will be described in more detail by way of the following examples. However, the present invention shall not be limited to the examples. A "parts" in the examples shows "parts by weight", unless otherwise specified.

Example 1

Synthesis an Aminium Salt of Compound No.1

Substitution Reaction 2.2 parts of N,N,N',N'-tetrakis(aminophenyl)-p-phenylene diamine and 12 parts of 4-bromobutylonitrile were added in 16 parts of DMF, followed by reacting at 130° C. for 10 hrs, cooling and filtering. 40 parts of methanol was added to the reaction solution, followed by stirring at 5° C. and below for 1 hr. The deposited crystal was filtrated, washed with methanol and dried to obtain 2.8 parts of light brown crystal.

Oxidation Reaction 1.0 part of N,N,N',N'-tetrakis {p-di(cyanopropyl) aminophenyl} -p-phenylene diamine was added in 14 parts of DMF, followed by heating at 60° C. to dissolve, adding 0.36 parts of silver hexafluoroantimonate dissolved in 14 parts of DMF, and reacting for 30 min. After cooling, the deposited silver was filtered out. 20 parts of water was dropped gradually in the reaction solution, followed by stirring for 15 min. The deposited green crystal was filtrated and washed with 50 parts of water to give a cake, which was then dried to obtain 1.4 parts of an aminium salt of compound No.1.

λmax: 420, 880, 1372 nm(acetone) Extinction coefficient: 21,700 Decomposition point: 297° C.(TG-DTA)

Silver perchlorate, silver hexafluorophosphate, and silver tetrafluoroborate were used in place of silver hexafluoroantimonate in the same procedure as described in this example to obtain compound No.2, compound No.4, and compound No.5 respectively.

Compound No.2

λmax: 418, 884, 1370 nm(acetone) Extinction coefficient: 18,900 Decomposition point: 235° C.(TG-DTA)

Compound No.4

λmax: 418, 890, 1368 nm(acetone) Extinction coefficient: 21,200 Decomposition point: 228° C.(TG-DTA)

The Compound No.5

λmax: 420, 880, 1376 nm(acetone) Extinction coefficient: 19,600 Decomposition point: 335° C.(TG-DTA)

11 parts of 3-bromopropionitrile and 13 parts of 5-bromopentylonitrile were used in place of 12 parts of 4-bromobutylonitrile in the same procedure as described in this example to obtain Compound No.7 and Compound No.9 respectively.

Equal moles of bromobutane and then 3 times moles of 3-propionitrile relative to N, N, N', N'-tetrakis(aminophenyl) -p-phenylene diamine were used in place of 12 parts of 4-bromobutylonitrile in the same procedure as described in this example to obtain Compound No.12.

Example 2

Synthesis an Aminium Salt of Compound No.6

The synthesis was carried out in the same procedure as described in Example 1, except that silver nitrate was used in place of the silver hexafluoroantimonate and further 1,5-dinaphthalene sulfonic acid was added into the reaction solution to react. One part of an aminium salt of Compound No.6 was obtain.

λmax: 420, 886, 1320 nm(acetonitrile) Extinction coefficient: 25,700 Decomposition point: 161° C.(TG-DTA)

p-toluene sulfonic acid was used in place of 1,5-dinaphthalene sulfonic acid in the same procedure as described in this example to obtain an aminium salt of Compound No.3,.

The aminium salts of the present invention shown in Table 1 to 3 were synthesized by the almost same procedures as described in Example 1 or 2: that is, by carrying out the substitution reactions to synthesize their corresponding phenylenediamines, which were then either oxidized for example with their corresponding silver salts or oxidized with the above oxidizing agents followed by reacting with their corresponding anions.

Example 3

Synthesis of a Diimonium Salt of Compound No.38,

Substitution Reaction 2.2 parts of N,N,N',N'-tetrakis(aminophenyl)-p-phenylene diamine and 12 parts of 4-bromobutylonitrile were added in 16 parts of DMF, followed by reacting at 130° C. for 10 hrs, cooling and filtering. 40 parts of methanol was added to the reaction solution, followed by stirring at 5° C. and below for 1 hr. The deposited crystal was filtrated, washed with methanol and dried to obtain 2.8 parts of light brown crystal.

Oxidation Reaction 1.0 part of N,N,N',N'-tetrakis {p-di(cyanopropyl) aminophenyl}-p-phenylene diamine was added in 14 parts of DMF, followed by heating at 60° C. to dissolve, adding 0.73 parts of silver hexafluoroantimonate dissolved in 14 parts of DMF, and reacting for 30 min. After cooling, the deposited silver was filtered out. 20 parts of water was dropped gradually in the reaction solution, followed by stirring for 15 min. The deposited black crystal was filtrated and washed with 50 parts of water to give a cake, which was then dried to obtain 1.4 parts of Compound No.38.

$\lambda$max: 1042 nm(acetonitrile) Extinction coefficient: 89,000 Decomposition point: 235° C.(TG-DTA)

11 parts of 3-bromopropionitrile and 13 parts of 5-bromopentylonitrile were used in place of 12 parts of 4-bromobutylonitrile in the same procedure as described in this example to obtain Compound No. 44 and Compound No. 46 respectively. Compound No.46

$\lambda$max: 1084 nm(dichloromethane) Extinction coefficient: 96,000 Decomposition point: 253° C.(TG-DTA)

Equal moles of bromobutane and then 3 times moles of 3-propionitrile relative to N, N, N', N'-tetrakis (aminophenyl)-p-phenylene diamine were used in place of 12 parts of 4-bromobutylonitrile in the same procedure as described in this example to obtain a diiimmonium salt of Compound No.49.

Example 4

Synthesis of a Diimonium Salt of Compound No.39

The synthesis was carried out in the same procedure as described in Example 3, except that silver perchlorate was used in place of the silver hexafluoroantimonate, to obtain 1.4 part of Compound No.39.

$\lambda$max: 1042 nm(acetonitrile) Extinction coefficient: 87,000 Decomposition point: 254° C.(TG-DTA)

Silver hexafluorophosphate and silver tetrafluoroborate were used in place of silver perchlorate in the same procedure as described in this example to obtain Compound No. 41 and Compound No.42, respectively.

Compound No.41

$\lambda$max: 1042 nm( acetonitrile) Extinction coefficient: 90,000 Decomposition point: 240° C.(TG-DTA) Compound No.42

$\lambda$max: 1042 nm(acetonitrile) Extinction coefficient: 87,000 Decomposition point: 214° C. (TG-DTA)

Example 5

Synthesis of a Diimonium Salt of Compound No.43

The synthesis was carried out in the same procedure as described in Example 3, except that silver nitrate was used in place of the silver hexafluoroantimonate and further 1,5-dinaphthalene sulfonic acid was added into the reaction solution to react, to obtain 1.0 part of Compound No.43.

$\lambda$max: 1042 nm(acetonitrile) Extinction coefficient: 90,000 Decomposition point: 238° C.(TG-DTA)

p-toluene sulfonic acid was used in place of 1,5-dinaphthalene sulfonic acid in the same procedure as described in this example to obtain a diimonium salt of Compound No.40

The diimonium salts of the present invention shown in Table 4 to 6 were synthesized by the almost same procedures as described in Example 3–5: that is, by carrying out the substitution reactions to synthesize their corresponding phenylenediamines, which were then either oxidized f or example with their corresponding silver salts or oxidized with the above oxidizing agents followed by reacting with their corresponding anions.

Example 6

Recording Medium 0. 02 parts of an aminium salt of Compound No. 1, obtained i n Example 1 and 0.10 part of the cyanine dyestuff(OM-57, made by Fujifilm KK) were dissolved in 10 parts of tetrafluoropropanol, and passed through a 0.2 $\mu$m filter to obtain a coating solution. 5 ml of this solution was dropped on a grooved 5 inched polycarbonate resin substrate by a pipette, coated by a spin coater and dried to form an organic thin membrane recording layer. The maximum absorption wavelength of the coated membrane was 719 nm. Gold was coated over the coated membrane by sputtering to make a reflection layer. The optical recording medium thus obtained was evaluated by using a CD-R regenerator, showing that it could record and regenerate.

Example 7

Recording Medium 0.02 parts of a diimonium salt of Compound of No.38 obtained in Example 3 and 0.10 part of the cyanine dyestuff (OM-57, made by Fuji film KK)were dissolved in 0.10 parts of tetrafluoropropanol, and passed through a 0.2 $\mu$m filter to obtain a coating solution. 5 ml of this solution was dropped on a grooved 5 inched polycarbonate resin substrate by a pipette, coated by a spin coater and dried to form an organic thin membrane recording layer. The maximum absorption wavelength of the coated membrane was 719 nm. Gold was coated over the coated membrane by sputtering to make a reflection layer. The optical recording medium thus obtained was evaluated by using a CD-R regenerator, showing that it could record and regenerate.

Example 8

Infrared Ray Screening Filter, Light Fastness Test, Heat Fastness Test 0.1 part of a diimonium salt of Compound No.38, obtained in Example 1 was dissolved in 10 parts of tetrafluoropropanol. 1 mg of this solution was spin-coated over a polycarbonate base plate at a rotation speed of 2000 rpm to obtain an infrared ray screening filter of the present invention (Example 8-1). Compound No. 39, Compound No. 41, Compound No.43 and Compound No. 46 were used in place of Compound No.38 in the same procedure as described above to obtain their respective infrared ray screening filters (Example 8-2), (Example 8-3), (Example 8-4) and (Example 8-5).

The infrared ray screening filters were set in the ultraviolet long life carbon arc light fastness tester(made by Suga Tester KK) at a black panel temperature of 63° C. and exposed to light from the base plate for 5 hrs, 10 hrs and 20 hrs to test light fastness.

Furthermore, the infrared ray screening filters were set in a hot-air drier at 80° C. for 1 day, 4 days and 7 days to test heat fastness. The residual dyestuff percentages were determined by a spectrophotometer.

An infrared ray screening filter for the comparative example was prepared to evaluate by the same procedure as described above, except that tetrakis {p-di(n-butyl) aminophenyl} phenylene diimonium hexafluoroantimonate was used in place of a diimonium salt of Compound of No.38.

The results of light fastness test and heat fastness test are shown in Table 7 and Table 8 respectively.

TABLE 7

(Light fastness test)

Residual Dyestuff Percentage (%)

| Example No. | Start | 10 hrs after | 20 hrs after |
|---|---|---|---|
| 8-1 | 100 | 94.1 | 82.4 |
| 8-2 | 100 | 88.4 | 85.8 |
| 8-3 | 100 | 90.7 | 88.4 |
| 8-4 | 100 | 83.8 | 77.2 |
| 8-5 | 100 | 92.4 | 87.2 |
| Comparative | 100 | 77.0 | 70.8 |

TABLE 8

(Heat fastness test)

Residual Dyestuff Percentage (%)

| Example No. | Start | 1 Day after | 4 Days after | 7 Days after |
|---|---|---|---|---|
| 8-1 | 100 | 90.3 | 83.1 | 74.7 |
| 8-2 | 100 | 93.5 | 91.1 | 86.4 |
| 8-3 | 100 | 95.7 | 89.2 | 78.2 |
| 8-4 | 100 | 94.7 | 68.8 | 22.2 |
| 8-5 | 100 | 83.0 | 63.6 | 47.4 |
| Comparative | 100 | 75.0 | 16.7 | 9.2 |

Example 9

Infrared Ray Screening Filter

A diimonium salt of compound No.38, was added in PMMA (polymethylmethacrylate)by 0.03% relative to the PMMA, which was then molded by injection at 200° C. to obtain two filters having their respective thickness of 1 mm and 3 mm. Average light transmissions of the filters in a region of 800–1000 nm were determined by a spectrophotometer. The 1 mm thick filter and the 3 mm thick filter showed 20% and 3% respectively.

Example 10

Light Fastness Test 0.1 part of the cyanine dyestuff (OM-57) was dissolved in 10 parts of tetrafluoropropanol. To the solution, 0.01 part of an aminium salt of Compound No.1 (Sample 1) and an aminium salt of Compound No.6 (Sample 2) were added to prepare their respective coating solutions. These solutions were spin-coated over polycarbonate base plates to prepare the dyestuff membranes. The dyestuff membranes were set in the ultraviolet long life carbon arc light fastness tester (made by Suga Tester KK) at a black panel temperature of 63° C. and exposed to light from the base plate for 5 hrs, 10 hrs and 20 hrs to test light fastness. The residual percentages of the cyanine dyestuff were determined by a spectrophotometer. The results are shown in Table 9. A dyestuff membrane for the comparative example was prepared to evaluate by the same procedure as described above except that tetrakis {p-di(n-butyl)aminophenyl} phenylene aminium hexafluoroantimonate (Comparative sample 1) was used in place of an aminium salt of Compound No.1. The results are shown in Table 9.

TABLE 9

(Light fastness test)

Residual Percentage of cyanine dyestuff (%)

| Sample No. | Start | 5 hrs after | 10 hrs after | 20 hrs after |
|---|---|---|---|---|
| 1 | 100 | 83 | 72 | 30 |
| 2 | 100 | 84 | 77 | 60 |
| Comparative 1 | 100 | 81 | 69 | 16 |

Example 11

Infrared Ray Screening Filter, Light Fastness Test, Heat Fastness Test 0.1 part of an aminium salt of Compound No.1 obtained in Example 1 was dissolved in 10 parts of tetrafluoropropanol. 1 mg of this solution was spin-coated over a polycarbonate base plate at a rotation speed of 2000 rpm to obtain the infrared ray screening filter of the present invention.

The infrared ray screening filter was set in the ultraviolet long life carbon arc light fastness tester(made by Suga Tester KK) at a black panel temperature of 63° C. and exposed to light from the base plate for 10 hrs and 20 hrs to test light fastness. Furthermore, the infrared ray screening filter was set in a hot-air drier at 80° C. for 1 day and 7 days to test heat fastness. The residual dyestuff percentages were determined by a spectrophotometer. The results of light fastness test and heat fastness test are shown in Table 10 and Table 11 respectively.

An infrared ray screening filter for the comparative example was prepared to evaluate by the same procedure as described above, except that tetrakis {p-di(n-butyl) aminophenyl} phenylene aminium hexafluoroantimonate was used in place of an aminium salt of Compound No.1.

TABLE 10

(Light fastness test)

Residual percentage of aminium (%)

| Example No. | Start | 10 hrs after | 20 hrs after |
|---|---|---|---|
| 11 | 100 | 90.0 | 85.6 |
| Comparative | 100 | 80.1 | 55.5 |

TABLE 11

(Heat fastness test)

Residual percentage of aminium (%)

| Example No. | Start | 1 Day after | 7 Days after |
|---|---|---|---|
| 11 | 100 | 95.0 | 70.6 |
| Comparative | 100 | 31.5 | Color change |

Example 12

Light Fastness Test 0.1 part of the cyanine dyestuff (OM-57) was dissolved in 10 parts of tetrafluoropropanol. To the solution, 0.01 part of a diimonium salt of Compound No.38 (Sample 1) obtained in Example 3 and a diimonium salt of Compound No.39 (Sample 2) were added to prepare their respective coating solutions. These solutions were spin-coated over polycarbonate base plates to prepare the dyestuff membranes.

The dyestuff membranes were set in the ultraviolet long life carbon arc light fastness tester(made by Suga Tester KK) at a black panel temperature of 63° C. and exposed to light from the base plate for 5 hrs and 20 hrs to test light fastness.

The residual percentages of the cyanine dyestuff were determined by a spectrophotometer. The results are shown in Table 12. A dyestuff membrane for the comparative example was prepared to evaluate by the same procedure as described above except that tetrakis {p-di(n-butyl)aminophenyl} phenylenediimonium hexafluoroantimonate(Comparative sample 1) was used in place of Compound No.38.

TABLE 12

(Light fastness test)

Residual Percentage of cyanine dyestuff (%)

| Sample No. | Start | 5 hrs after | 20 hrs after |
|---|---|---|---|
| 1 | 100 | 81 | 59 |
| 2 | 100 | 80 | 37 |
| Comparative 1 | 100 | 81 | 16 |

Example 13

Heat Fastness Test 0.1 part of a diimonium salt of compound No.38 obtained in Example 3 was dissolved in 10 parts of tetrafluoropropanol. This solution was spin-coated over a polycarbonate base plate to prepare the recording membrane (Sample 3).

The recording membrane was set in a hot-air drier at 80° C. for 1 day, 4 days and 7 days to test heat fastness. The residual dyestuff percentages of a diimonium salt of Compound No.38 were determined by a spectrophotometer.

A recording membrane for the comparative example was prepared to evaluate by the same procedure as described above except that tetrakis {p-di(n-butyl)aminophenyl } phenylene diimonium hexafluoroantimonate (Comparative sample 2)was used in place of a diimonium salt of Compound No.38.

The results of heat fastness test are shown in Table 13.

TABLE 13

(Heat fastness test)

Residual percentage of diimonium (%)

| Sample No. | Start | 1 Day after | 4 Days after | 7 Days after |
|---|---|---|---|---|
| 3 | 100 | 90.3 | 83.1 | 74.7 |
| Comparative 3 | 100 | 75.0 | 16.7 | 9.2 |

Industrial Applicability

An aminium salt or diimonium salt compound of the present invention can be used as a material for the recording layer in an optical recording medium, because they have the maximum absorption wavelengths in the region of 900 nm or more and are excellent in heat fastness and light fastness. The aminium salt or diimonium salt compound of the present invention, if contained in an organic dyestuff thin layer that is the recording layer of an optical recording medium for example, can also provide the optical recording medium with increased durability and light fastness in a repeated regeneration, because they can improve the light fastness of the organic dyestuff. Furthermore, the aminium salt or diimonium salt compound of the present invention can be used for an infrared ray screening film, a heat insulating film and a sunglass, because they have their maximum absorptions in the infrared region and are excellent in heat fastness and light fastness.

What is claimed is:

1. An aminium salt or diimonium salt compound consisting the aminium or diimonium cation and an anion, said aminium cation having a skeletal structure represented by Formula (1) as described below:

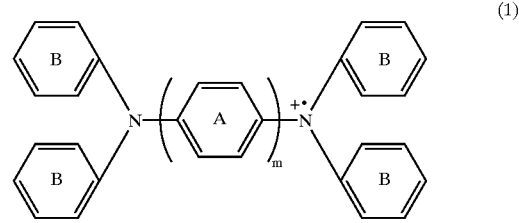

(1)

(in the formula (1), m is an integer of 1 or 2),
said diimonium cation having a skeletal structure represented by Formula (2) as described below:

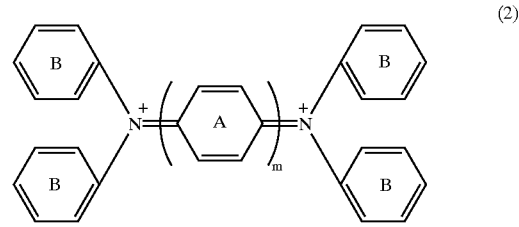

(2)

(in the formula (2), m is an integer of 1 or 2),
wherein the two nitrogen atoms (quaternary nitrogen atoms in Formula (2)) bound to the ring A in Formula (1) or Formula (2) bind to the four phenyl groups B, and wherein the phenyl groups B are optionally each substituted at their respective 4-positions with an amino group, and at least one of said four amino groups has a cyanoalkyl group as a substituent.

2. An aminium salt or diimonium salt compound according to claim 1, wherein said cyanoalkyl group is a cyano (C1–C5) alkyl group.

3. An aminium salt or diimonium salt compound according to claim 1 or 2, wherein all of said four amino groups are substituted with a respective cyanoalkyl group.

4. An aminium salt or diimonium salt compound according to claim 3, wherein said amino groups having said cyanoalkyl groups are di(cyanoalkyl)amino groups.

5. An aminium salt or diimonium salt compound according to claim 4, wherein said cyanoalkyl groups are cyanopropyl groups.

* * * * *